United States Patent [19]

Rodewald

[11] 4,090,981

[45] May 23, 1978

[54] CATALYST FOR SELECTIVE PRODUCTION OF PARA DIALKYL SUBSTITUTED BENZENES

[75] Inventor: Paul G. Rodewald, Rocky Hill, N.J.

[73] Assignee: Mobile Oil Corporation, New York, N.Y.

[21] Appl. No.: 726,091

[22] Filed: Sep. 23, 1976

[51] Int. Cl.² ............................................. B01J 29/06
[52] U.S. Cl. ..................................... 252/455 Z; 55/75
[58] Field of Search ......................... 252/455 Z; 55/75

[56] References Cited

U.S. PATENT DOCUMENTS

| 2,722,504 | 11/1955 | Fleck | 208/110 |
| 3,751,504 | 8/1973 | Keown et al. | 252/455 Z |
| 3,980,586 | 9/1976 | Mitchell | 252/455 Z |

*Primary Examiner*—Carl F. Dees
*Attorney, Agent, or Firm*—Charles A. Huggett; Raymond W. Barclay

[57] ABSTRACT

A catalyst particularly applicable for the selective production of para dialkyl substituted benzenes is provided comprising a porous crystalline aluminosilicate zeolite which has undergone modification by deposition thereon of a coating of silica extensively covering, and residing substantially exclusively on the external surface thereof as a result of contact with a silicone compound of a molecular size incapable of entering the pores of the zeolite and subsequent heating in an oxygen-containing atmosphere to a temperature in excess of 300° C. but below a temperature at which crystallinity of the zeolite is adversely affected at a rate such that the silicone compound does not volatilize prior to undergoing oxidation to silica. The zeolite is characterized by an activity, in terms of alpha value, of between about 2 and about 5000, a xylene sorption capacity greater than 1 gram/100 grams of zeolite and an ortho-xylene sorption time for 30 percent of said capacity of greater than 10 minutes, said sorption capacity and sorption time being measured at 120° C. and a xylene pressure of 4.5 ± 0.8 mm. of mercury.

11 Claims, No Drawings

CATALYST FOR SELECTIVE PRODUCTION OF PARA DIALKYL SUBSTITUTED BENZENES

BACKGROUND OF THE INVENTION

1. Field of the Invention

This invention relates to a catalyst suitable for the selective production of para dialkyl substituted benzenes and to a process for converting specified charge stocks to a high yield of para dialkyl substituted benzenes utilizing such catalyst.

2. Description of the Prior Art

The disproportionation of aromatic hydrocarbons in the presence of zeolite catalysts has been described by Grandio et al. in the Oil and Gas Journal, Vol. 69, No. 48 (1971). U.S. Pat. Nos. 3,126,422; 3,413,374; 3,598,878; 3,598,879 and 3,607,961 show vapor-phase disproportionation of toluene over various catalysts.

In these prior art processes, the xylene product produced has the equilibrium composition of approximately 24 percent para, 54 percent meta and 22 percent ortho.

In addition to the above patents, other related prior art includes U.S. Pat. No. 2,904,607 which refers to alkylation of aromatic hydrocarbons with an olefin in the presence of a crystalline metallic aluminosilicate having uniform pore openings of about 6 to 15 Angstrom units. U.S. Pat. No. 3,251,897 describes alkylation of aromatic hydrocarbons in the presence of X- or Y-type crystalline aluminosilicate zeolites, specifically such type zeolites wherein the cation is rare earth and/or hydrogen. U.S. Pat. Nos. 3,751,504 and 3,751,506 describes vapor phase alkylation of aromatic hydrocarbons with olefins, e.g. benzene with ethylene, in the presence of a ZSM-5 type zeolite catalyst.

The alkylation of toluene with methanol in the presence of a cation exchanged zeolite Y has been described by Yashima et al. in the Journal of Catalysis 16, 273-280 (1970). The workers reported selective production of paraxylene over the approximate temperature range of 200° to 275° C., with the maximum yield of para-xylene in the mixture of xylenes, i.e. about 50 percent of the xylene product mixture being observed at 225° C. Higher temperatures were reported to result in an increase in the yield of meta-xylene and a decrease in the production of para and ortho-xylenes. U.S. Pat. No. 3,965,210 describes alkylation of toluene with methanol in the presence of a crystalline aluminosilicate zeolite, such as ZSM-5, which has been modified by contact with a polymer made up of meta-carborane units connected by siloxane units to selectively yield para-xylene. These latter catalysts have, however, suffered from the serious deficiency of loss of selectivity upon air regeneration. This is attributable to breakage of carbon-silicon bonds upon exposure to the high temperature of regeneration giving rise to isolated clusters of silica on the zeolite surface rather than the extensive surface coverage afforded by the technique described herein.

U.S. Pat. No. 2,722,504 describes a catalyst of an activated oxide such as silica gel having a thin layer of a silicone polymer deposited thereon to increase the organophilic character of the contact surface and, as such, seeks to avoid silica deposition.

Crystalline aluminosilicate zeolites, modified by reaction with an organic substituted silane, have been described in U.S. Pat. Nos. 3,682,996 and 3,698,157. The former of these patents describes, as novel compositions of matter, crystalline aluminosilicate esters made by reacting a crystalline aluminosilicate having an available hydrogen atom with an organic silane having a SiH group. The resulting compositions were disclosed as being catalysts useful for hydrocarbon processes, particularly hydrocracking. In the latter of the above patents, the use of ZSM-5 type crystalline aluminosilicate zeolites modified by treatment with an organic-radical substituted silane are described, together with the use of such modified zeolites in chromatographic separation of the compounds in a $C_8$ aromatic feed stock.

While the above-noted prior art is considered of interest in connection with the subject matter of the present invention, the conversion process described herein utilizing a catalyst of particularly defined sorption properties comprising a crystalline aluminosilicate zeolite characterized by an alpha value of between 2 and about 5000 modified by a coating of silica derived from a silicone, has not, insofar as is known, been heretofore described.

Of the xylene isomers, i.e. ortho, meta and para-xylene, meta-xylene is the least desired product, with ortho and para-xylene being the more desired products. Para-xylene is of particular value being useful in the manufacture of terephthalic acid which is an intermediate in the manufacture of synthetic fibers, such as "Dacron". Mixtures of xylene isomers, either alone or in further admixture with ethylbenzene, generally containing a concentration of about 24 weight percent para-xylene in the equilibrium mixture, have previously been separated by expensive superfractionation and multistage refrigeration steps. Such process, as will be realized, has involved high operation costs and has a limited yield.

SUMMARY OF THE INVENTION

In accordance with the present invention, there has been discovered a catalyst, particularly applicable for the selective production of para-dialkyl substituted benzenes, comprising a porous crystalline aluminosilicate zeolite having deposited thereon a coating of silica extensively covering the surface of said zeolite. The coating of silica is substantially exclusively on the external surface of the zeolite as a result of contact of the latter with a silicone compound of a molecular size incapable of entering the pores thereof, followed by heating in an oxygen-containing atmosphere, such as air, to a temperature in excess of 300° C. but below a temperature at which crystallinity of the zeolite is adversely affected at a rate such that the silicone compound does not volatilize prior to undergoing oxidation to silica. The zeolite employed has an activity, in terms of alpha value, of between about 2 and about 5000, a xylene sorption capacity greater than 1 gram/100 grams of zeolite and an ortho-xylene sorption time, hereinafter described, for 30 percent of such capacity of greater than 10 minutes, the sorption capacity and sorption time being measured at 120° C. and a xylene pressure of 4.5 ± 0.8 mm. of mercury. The resulting catalyst has been found to possess a long catalytic life, e.g. to be capable of regeneration after catalytic use without substantial loss in activity.

The above catalyst has been found to be particularly useful in the selective production of para dialkyl substituted benzenes containing alkyl groups of 1 to 4 carbon atoms, such as para-xylene, by conversion in the presence thereof, of a hydrocarbon precursor such as a mono alkyl-substituted benzene having 1-4 carbon atoms in the alkyl substituent or a mixture of such precursor or benzene with an alkylating agent containing from 1 to 4 carbon atoms. Typical of the above conversion processes are the disproportionation of toluene and the alkylation of benzene or toluene with a methylating agent, e.g. methanol.

In a preferred embodiment, the present process comprises conversion of the specified precursor reactants to yield xylenes in which the proportion of para-xylene is substantially in excess of the normal equilibrium concentration and preferably in excess of 40 weight percent of the xylene product produced in the presence of the specified catalyst at a temperature between about 250° and about 750° C. at a pressure between about 0.1 and about 100 atmospheres utilizing a feed weight hourly space velocity (WHSV) between about 0.1 and about 2000. The latter WHSV is based upon the weight of catalyst compositions, i.e. total weight of active catalyst and binder therefor. The effluent is separated and distilled to remove the desired product, e.g. para-xylene and unreacted material is recycled for further reaction.

DESCRIPTION OF SPECIFIC EMBODIMENTS

The zeolite base component of the present catalyst upon which silica deposition is effected is characterized by particular activity and sorption properties. Thus, the porous crystalline aluminosilicate zeolite employed herein necessarily has: (1) an activity, in terms of alpha value, of between about 2 and about 5000, (2) a xylene sorption capacity greater than 1 gram/100 grams of zeolite and (3) an ortho-xylene sorption time for 30 percent of said capacity of greater than 10 minutes, where the sorption capacity and sorption time are measured at 120° C. and a xylene pressure of 4.5 ± 0.8 mm. of mercury.

The alpha value reflects the relative activity of the catalyst with respect to a high activity silica-alumina cracking catalyst. To determine the alpha value as such term is used herein, n-hexane conversion is determined at about 1000° F. Conversion is varied by variation in space velocity such that a conversion level of 10 to 60 percent of n-hexane is obtained and converted to a rate constant per unit volume of zeolite and compared with that of silica-alumina catalyst which is normalized to a reference activity of 1000° F. Catalytic activity of the catalysts are expressed as multiple of this standard, i.e. the silica-alumina standard. The silica-alumina reference catalyst contains about 10 weight percent $Al_2O_3$ and remainder $SiO_2$. This method of determining alpha, modified as described above, is more fully described in the Journal of Catalysis, Vol. VI, Pages 278-287, 1966.

The measurements of hydrocarbon sorption capacities and rates are conveniently carried out gravimetrically in a thermal balance. In particular, it has been found that an equilibrium sorption capacity of xylene, which can be either para, meta, ortho or a mixture thereof, preferably para-xylene since this isomer reaches equilibrium within the shortest time of at least 1 gram per 100 grams of zeolite measured at 120° C. and a xylene pressure of 4.5 ± 0.8 mm of mercury and an orthoxylene sorption time for 30 percent of said capacity of greater than 10 minutes (at the same conditions of temperature and pressure) are required in order to achieve the desired selective production of para dialkyl substituted benzenes.

It has been found that zeolites exhibiting very high selectivity for para-dialkylbenzene production require a very long time up to and exceeding a thousand minutes to sorb o-xylene in an amount of 30% of total xylene sorption capacity. For those materials it is more convenient to determine the sorption time for a lower extent of sorption, such as 5%, 10% or 20% of capacity, and to estimate the 30% sorption time by applying the following multiplication factors F as illustrated for 5% sorption:

| $t_{0.3} = F \cdot t_{0.05}$ Percent of sorption capacity | Factor(F) to Estimate 30% Sorption Time |
|---|---|
| 5 | 36 |
| 10 | 9 |
| 20 | 2.2 |

Zeolites such as zeolite X, zeolite Y, ZSM-4, faujasite, mordenite, ferrierite and offretite which satisfy the aforenoted activity and sorption characteristics are within the confines of this invention. Particularly preferred are those zeolites having a silica to alumina ratio of at least about 12 and a constraint index within the approximate range of 1 to 12. These zeolites induce profound transformation of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio preferred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is exclued and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F for at least 15 minutes. The zeolite is then flushed with helium and the temperature adjusted between 550° F and 950° F to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "contraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.4 |
| REY | 0.4 |
| Amorphous Silica-Alumina | 0.6 |

-continued

| CAS | C.I. |
|---|---|
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F to 950° F, with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest in approximate, taking into consideration the manner of its determination, with probability, in some instances of compounding variable extremes. However, in all instances, at a temperature within the above-specified range of 550° F to 950° F, the constraint index will have a value for any given zeolite of interest herein within the approximate range of 1 to 12.

The class of zeolites defined herein is exemplified by ZSM-5, ZSM-11, ZSM-12, ZSM-35, ZSM-38, and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-38 is more particularly described in U.S. application Ser. No. 528,060, filed Nov. 29, 1974. This zeolite can be identified, in terms of mole ratios of oxides and in the anhydrous state, as follows:

$$(0.3-2.5)R_2O : (0-0.8)M_2O : Al_2O_3 : > 8 SiO_2$$

wherein R is an organic nitrogen-containing cation derived from a 2-(hydroxyalkyl) trialkylammonium compound and M is an alkali metal cation, and is characterized by a specified X-ray power diffraction pattern.

In a preferred synthesized form, the zeolite has a formula, in terms of mole ratios of oxides and in the anhydrous state, as follows:

$$(0.4-2.5)R_2O : (0-0.6)M_2O : Al_2O_3 : xSiO_2$$

wherein R is an organic nitrogen-containing cation derived from a 2-(hydroxyalkyl)trialkylammonium compound, wherein alkyl is methyl, ethyl or a combination thereof, M is an alkali metal, especially sodium, and x is from greater than 8 to about 50.

The synthetic ZSM-38 zeolite possesses a definite distinguishing crystalline structure whose x-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33A.

TABLE I

| d (A) | I/Io |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-38 is its sorptive capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-38 (after calcination at 600° C.) is less than 10, whereas that ratio for the natural ferrierite is substantially greater than 10, for example, as high as 34 or higher.

Zeolite ZSM-38 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| | Broad | Preferred |
|---|---|---|
| $\frac{R+}{R+ + M+}$ | 0.2–1.0 | 0.3–0.9 |
| $OH^-/SiO_2$ | 0.05–0.5 | 0.07–0.49 |
| $H_2O/OH^-$ | 41–500 | 100–250 |
| $SiO_2/Al_2O_3$ | 8.8–200 | 12–60 | wherein R is an organic nitrogen-containing cation derived from a 2-(hydroxyalkyl) trialkylammonium compound and M is an alkali metal ion, and maintaining the mixture until crystals of the zeolite are formed. (The quantity of $OH^-$ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F. for from about 8 to 24 hours.

ZSM-35 is more particularly described in U.S. Application Ser. No. 528,061, filed Nov. 29, 1974. This zeolite can be identified, in terms of mole ratios of oxides and in the anhydrous state, as follows:

$$(0.3-2.5)R_2O : (0-0.8)M_2O : Al_2O_3 : > 8 \ SiO_2$$

wherein R is an organic nitrogen-containing cation derived from ethylenediamine or pyrrolidine and M is an alkali metal cation, and is characterized by a specified X-ray powder diffraction pattern.

In a preferred synthesized form the zeolite has a formula, in terms of mole ratios of oxides and in the anhydrous state, as follows:

$$(0.4-2.5)R_2O : (0.0.6) \ M_2O : Al_2O_3 : xSiO_2$$

wherein R is an organic nitrogen-containing cation derived from ethylenediamine or pyrrolidine, M is an alkali metal, especially sodium, and x is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3–11.5A. This very weak line, however, is determined not to be a significant line for ZSM-35.

TABLE II

| d (A) | I/Io |
|---|---|
| 9.6 ± 0.20 | Very Strong-Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600° C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH$^-$/SiO$_2$ | 0.05–0.5 | 0.07–0.49 |
| H$_2$O/OH$^-$ | 41–500 | 100–250 |
| SiO$_2$/Al$_2$O$_3$ | 8.8–200 | 12–60 | wherein R is an organic nitrogen-containing cation derived from pyrrolidine or ethylenediamine and M is an alkali metal ion, and maintaining the mixture until crystals of the zeolite are formed. (The quantity of OH$^-$ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such a range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F., for from about 8 to 24 hours.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35, with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred zeolites of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, −11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel copper, zinc, palladium, calcium or rare earths metals.

In practicing the desired conversion process, it may be desirable to incorporate the above described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

In accordance with this invention, a porous crystalline aluminosilicate zeolite, as above characterized, has a coating of silica deposited thereon. Such coating extensively covers the external surface of the zeolite and resides substantially completely on the external surface. The coating of silica is deposited on the surface of the zeolite by contacting the latter with a silicone compound molecular size incapable of entering the pores of the zeolite and subsequently heating in an oxygen-containing atmosphere, such as air, to a temperature above 300° C. but below a temperature at which the crystallinity of the zeolite is adversely affected at a rate such that the silicone compound does not volatilize before undergoing oxidation of silica.

The silicone compound utilized to effect the silica coating is characterized by the general formula:

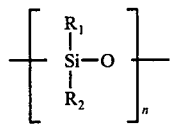

where $R_1$ is hydrogen, fluorine, hydroxy, alkyl, aralkyl, alkaryl or fluoro-alkyl. The hydrocarbon substituents generally contain from 1 to 10 carbon atoms and preferably are methyl or ethyl groups. $R_2$ is selected from the same group as $R_1$, other than hydrogen and $n$ is an integer of at least 10 and generally in the range of 10 to 1000. The molecular weight of the silicone compound employed is generally between about 500 and about 20,000 and preferably within the approximate range of 1000 to 10,000. Representative silicone compounds include dimethylsilicone, diethylsilicone, phenylmethylsilicone, methylhydrogensilicone, ethylhydrogensilicone, phenylhydrogensilicone, methylethylsilicone, phenylethylsilicone, diphenylsilicone, methyltrifluoropropylsilicone, ethyltrifluoropropylsilicone, polydimethylsilicone, tetrachlorophenylmethyl silicone, tetrachlorophenylethyl silicone, tetrachlorophenylhydrogen silicone, tetrachlorophenylphenyl silicone, methylvinylsilicone and ethylvinylsilicone.

The silicone compound dissolved in a suitable solvent therefor, e.g., n-hexane, pentane, heptane, benzene, toluene, chloroform, carbon tetrachloride, is contacted with the abovedescribed zeolite at a temperature between about 10° C. and about 100° C. for a period of time sufficient to deposit the ultimately desired amount of silicone thereon. Time of contact will generally be within the range of 0.2 to 5 hours, during which time the mixture is desirably subjected to evaporation. The resulting residue is then calcined in an oxygen-containing atmosphere, preferably air, at a rate of 0.2° to 5° C./minute to a temperature greater than 300° C. but below a temperature at which the crystallinity of the zeolite is adversely affected. Generally, such temperature will be below 600° C. Preferably the temperature of calcination is within the approximate range of 350° to 550° C. The product is maintained at the calcination temperature usually for 1 to 24 hours to yield a silica-coated zeolite containing between about 0.5 and about 30 weight percent and preferably between about 1 and 15 weight percent silica.

The charge stock used herein for the selective production of para dialkyl substituted benzenes containing alkyl groups of 1 to 4 carbon atoms by contact, under conversion conditions, with the above-described catalyst includes a hydrocarbon precursor selected from the group consisting of mono alkyl-substituted benzenes having 1-4 carbon atoms in the alkyl substituent, such as toluene, ethyl benzene, propyl benzene or butyl benzene and a mixture of such precursor or benzene with an alkylating agent containing from 1 to 4 carbon atoms.

Typical of the processes contemplated herein are disproportionation of toluene to benzene and xylene, wherein the proportion of para-xylene obtained is greatly in excess of its normal equilibrium concentration. Such process is effectively carried out at a temperature of between about 400° C. and about 700° C. at a pressure between 1 atmosphere and about 100 atmospheres utilizing a weight hourly space velocity of between about 1 and about 50.

The use of mixed aromatics as feed is also feasible. For example, a mixture of ethylbenzene and toluene is converted selectively to a mixture rich in p-diethylbenzene and p-ethyltoluene, the latter predominating at high toluene to ethylbenzene ratios in the feed.

Reaction of benzene, toluene, ethylbenzene, propylbenzene or butylbenzene with an alkylating agent containing from 1 to 4 carbon atoms is also contemplated using the catalyst described hereinabove. Suitable alkylating agents include olefins, alcohols, alkyl halides, ethers, sulfides having from 1 to 4 carbon atoms. Representative of such compounds are ethylene, propylene, butylene, methanol, ethanol, propanol, butanol, methyl chloride, ethyl chloride, propyl chloride, butyl chloride, dimethylether, dimethylsufide, diethylether, diethylsulfide, dipropylether, dipropylsulfide, dibutylether, and dibutylsulfide. Alkylation is suitably carried out at a temperature between about 250° C. and about 700° C. at a pressure between about 1 atmosphere and about 100 atmospheres employing a weight hourly space velocity of between about 0.1 and about 200.

It is contemplated that the conversion process described herein may be carried out as a batch type, semicontinuous or continuous operation utilizing a fixed or moving bed catalyst system. The catalyst after use is conducted to a regeneration zone wherein coke is burned from the catalyst in an oxygen-containing atmosphere, e.g. air, at an elevated temperature, after which the regenerated catalyst is recycled to the conversion zone for further contact with the charge stock. With use of the present silica-coated zeolite catalyst, regeneration has been found to restore the activity of the catalyst to a high level, thereby providing a long catalyst life. It is particularly feasible to conduct the desired conversion in the presence of hydrogen utilizing a hydrogen/hydrocarbon mole ratio of between about 2 and about 20, with hydrogen pressure extending from 1 atmosphere up to 100 atmospheres. The presence of hydrogen in the reaction zone has been found to very substantially reduce the aging rate of the catalyst.

While the above process has been described with reference to selective production of para dimethyl substituted benzenes, typified by para-xylene, it is contemplated that other para dialkyl substituted benzenes, wherein the alkyl group contains from 1 to 4 carbon atoms may similarly be selectively produced. Thus, utilizing the technique described herein, it is contemplated that with selection of suitable precursor, a mixture of ethyl benzene and toluene may be selectively converted to para ethyl toluene; ethyl benzene may be selectively converted to diethyl benzene, propyl benzene may be converted to dipropyl benzene and butyl benzene may be selectively converted to dibutylbenzenes.

The following examples will serve to illustrate the process and catalyst of the present invention without limiting the same.

EXAMPLE 1

To 1.42 grams of phenylmethylsilicone (molecular weight 1686) dissolved in 40 cc of n-hexane was added 4 grams of $NH_4$ ZSM-5 having a crystallite size of 1-2 microns. This sample of $NH_4$ ZSM-5 contained 35 percent alumina as a binder. The mixture was evaporated slowly over a 2-hour period using a rotary evaporator. The residue was calcined in air at 1° C/minute to 538° C. and then maintained at this temperature for 7 hours to yield silica-modified HZSM-5, containing 14 weight percent silica.

EXAMPLE 2

To 0.73 gram of phenylmethylsilicone (molecular weight 1686) dissolved in 40 cc of n-hexane was added 4 grams of $NH_4$ ZSM-5 having a crystallite size of 1-2 microns. The mixture was evaporated over 1/2 hour using a rotary evaporator. The residue was calcined in air at 1° C./minute to 538° C. and then maintained at this temperature for 7 hours to yield silica-modified HZSM-5, containing 7.5 weight percent silica.

EXAMPLE 3

To 0.32 gram of methylhydrogensilicone (molecular weight 3087) dissolved in 40 cc n-hexane was added 4 grams $NH_4$ ZSM-5 having a crystallite size of 1-2 microns. The mixture was evaporated over 1/2 hour using a rotary evaporator. The residue was calcined in air at 1° C./minute to 538° C. and maintained at this temperature for 7 hours to yield silica-modified HZSM-5, containing 7.5 weight percent silica.

EXAMPLE 4

To 0.40 grams dimethylsilicone (molecular weight 4385) dissolved in 40 cc n-hexane was added 4 grams $NH_4$ ZSM-5 having a crystallite size of 1-2 microns. The mixture was evaporated over 1/2 hour using a rotary evaporator. The residue was calcined in air at 1° C./minute to 538° C. and maintained at this temperature for 7 hours to yield silica-modified HZSM-5, containing 7.5 weight percent silica.

EXAMPLE 5

A sample of silica-modified HZSM-5 prepared as in Example 4 was pelleted, sized to 14-30 mesh and tested in a flow reactor for toluene disproportionation at atmospheric pressure and with flowing hydrogen, utilizing a hydrogen to hydrocarbon mole ratio of 2. Reaction was carried out at 550°-600° C. at weight hourly space velocities of 8-22. Results are summarized in Table III below.

TABLE III

| Catalyst | p-Xylene in Xylenes Wt.% | Toluene Conversion Wt.% | Weight Hourly Space Velocity | Temp., ° C. |
|---|---|---|---|---|
| Unmodified HZSM-5 | 33 | 20 | 20 | 550 |
| Fresh SiO$_2$/HZSM-5 | 65 | 7 | 22 | 550 |
|  | 56 | 12 | 11 | 550 |
|  | 46 | 20 | 8 | 550 |
| Regenerated SiO$_2$/HZSM-5 | 71 | 7 | 22 | 550 |
|  | 61 | 12 | 11 | 550 |
|  | 49 | 20 | 8 | 550 |
|  | 79 | 12 | 22 | 600 |
|  | 67 | 20 | 11 | 600 |

It will be seen from the above data that selectivity to para-xylene at the same conversion and temperature was significantly higher after modification with silica and that such selectivity remained high after regeneration of the catalyst by burning carbonaceous deposit therefrom in air at 540° C.

EXAMPLE 6

A sample of silica-modified HZSM-5 prepared as in Example 2 was pelleted, sized to 14-30 mesh and tested for toluene disproportionation at atmospheric pressure and with flowing hydrogen, utilizing a hydrogen to hydrocarbon mole ratio of 2. Reaction was carried out at a temperature of 550° C. at weight hourly space velocities of 6-25. Results are summarized in Table IV below.

TABLE IV

| Catalyst | p-Xylene in Xylenes, Wt.% | Toluene Conversion Wt.% | Weight Hourly Space Velocity | Temp., ° C. |
|---|---|---|---|---|
| Unmodified HZSM-5 | 33 | 20 | 20 | 550 |
| Fresh SiO$_2$/HZSM-5 | 92 | 7 | 25 | 550 |
|  | 90 | 12 | 13 | 550 |
|  | 84 | 20 | 6 | 550 |
| Regenerated SiO$_2$/HZSM-5 | 94 | 6 | 25 | 550 |
|  | 92 | 10 | 13 | 550 |
|  | 86 | 16 | 6 | 550 |

It will be evident from the foregoing results that the silica modified HZSM-5 catalyst is fully regenerable (in air at 540° C.) and shows significantly higher selectivity to para-xylene when compared with the unmodified catalyst at the same conversion and temperature.

EXAMPLE 7

A silica-modified HZSM-5 catalyst prepared in a manner similar to that of Example 2, but containing 1.9 weight percent silica was tested for toluene disproportionation in a flow reactor at atmospheric pressure and with flowing hydrogen, utilizing a hydrogen to hydrocarbon mole ratio of 2. Reaction was carried out at 550° C. at weight hourly space velocities of 5-20. Results are summarized in Table V below.

TABLE V

| p-xylene in xylenes, Wt.% | Toluene Conversion, Wt.% | Weight Hourly Space Velocity | Temp., °C. |
|---|---|---|---|
| 78 | 7 | 20 | 550 |
| 68 | 12 | 10 | 550 |
| 54 | 19 | 5 | 550 |

EXAMPLE 8

A sample of silica-modified HZSM-5 prepared as in Example 3 was tested for toluene disproportionation as in Example 7. Results are shown in Table VI below.

TABLE VI

| p-xylene in xylenes, Wt.% | Toluene Conversion, Wt.% | Weight Hourly Space Velocity | Temp., °C. |
|---|---|---|---|
| 80 | 11 | 20 | 550 |
| 66 | 20 | 10 | 550 |
| 53 | 28 | 5 | 550 |

EXAMPLE 9

Toluene disproportionation was carried out with a sample of a silica-modified HZSM-5 catalyst prepared as in Example 1. Reaction was conducted at 500° C. and 600 psig. The hydrogen to hydrocarbon mole ratio was 2 and the weight hourly space velocity was 7. During 18 days time on stream, the toluene conversion decreased slightly from 38 percent to 35 percent while the para-xylene in the xylene increased from 58 percent to 70 percent.

EXAMPLE 10

Alkylation of toluene with methanol was carried out in the presence of a sample of a silica-modified HZSM-5 prepared as in Example 2. The toluene to methanol mole ratio was 4 utilizing a pelleted catalyst, sized to 14–30 mesh. The reaction was carried out at a temperature of 400°–550° C. and atmospheric pressure at a weight hourly space velocity of 10 with flowing hydrogen, employing a hydrogen to hydrocarbon mole ratio of 2. The result summarized below in Table VII show high selectivity to para-xylene.

TABLE VII

| p-xylene in xylenes, Wt.% | Toluene Conversion, Wt.% | Weight Hourly Space Velocity | Temp., °C. |
|---|---|---|---|
| 88 | 84 | 10 | 550 |
| 91 | 60 | 10 | 500 |
| 94 | 44 | 10 | 450 |
| 95 | 36 | 10 | 400 |

It is to be understood that the foregoing description is merely illustrative of preferred embodiments of the invention, of which many variations may be made by those skilled in the art within the scope of the following claims without departing from the spirit thereof.

I claim:

1. A catalyst composition comprising a porous crystalline aluminosilicate zeolite having deposited thereon a coating of silica which extensively covers and resides substantially exclusively on the external surface thereof as a result of contact with a silicone compound of a molecular size incapable of entering the pores of the zeolite and subsequent heating in an oxygen-containing atmosphere to a temperature in excess of 300° C. but below a temperature at which crystallinity of the zeolite is adversely affected at a rate such that the silicone compound does not volatilize prior to undergoing oxidation to silica, said zeolite being characterized by an activity, in terms of alpha value, of between about 2 and about 5000, a xylene sorption capacity greater than 1 gram/100 grams of zeolite and an ortho xylene sorption time for 30 percent of said capacity greater than 10 minutes, said sorption capacity and sorption time being measured at 120° C. and a pressure of 4.5 ± 0.8 mm. of mercury.

2. The catalyst composition of claim 1 wherein said crystalline aluminosilicate zeolite has a silica to alumina ratio of at least about 12 and a constraint index within the approximate range of 1 to 12.

3. The catalyst composition of claim 1 wherein said crystalline aluminosilicate zeolite is ZSM-5.

4. The catalyst composition of claim 1 wherein said crystalline aluminosilicate zeolite is present in combination with a binder therefor.

5. The catalyst composition of claim 3 wherein ZSM-5 is predominately in the hydrogen form.

6. The catalyst composition of claim 1 wherein said coating of silica constitutes between about 0.5 and about 30 weight percent of the composition.

7. A method for making the catalyst composition of claim 1 wherein said zeolite is coated with silica by contact with a silicone compound of a molecular size incapable of entering the pores of the zeolite, said silicone compound having the general formula:

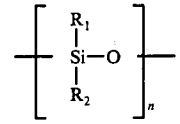

where $R_1$ is hydrogen, fluorine, hydroxy, alkyl, aralkyl, alkaryl, or fluoro-alkyl, the hydrocarbon substituents containing from 1 to 10 carbon atoms, $R_2$ is selected from the same group as $R_1$, other than hydrogen and $n$ is an integer of at least 10, and thereafter heating the resultant residue in an oxygen-containing atmosphere to a temperature in excess of 300° C. but below a temperature at which the crystallinity of the zeolite is adversely affected at a rate such that the silicone compound is not volatilized before undergoing oxidation to silica.

8. The method of claim 7 wherein said zeolite has a silica to alumina ratio of at least about 12 and a constraint index within the approximate range of 1 to 12.

9. The method of claim 7 wherein said zeolite is ZSM-5.

10. The method of claim 7 wherein said silicone is selected from the group consisting of dimethylsilicone, diethylsilicone, phenylmethylsilicone, methylhydrogensilicone, ethylhydrogensilicone, phenylhydrogensilicone, methylethylsilicone, phenylethylsilicone, diphenylsilicone, methyltrifluoropropylsilicone, ethyltrifluoropropylsilicone, polydimethylsilicone, tetrachlorophenylmethyl silicone, tetrachlorophenylethyl silicone, tetrachlorophenylhydrogen silicone, tetrachlorophenylphenyl silicone, methylvinylsilicone, and ethylvinylsilicone.

11. The method of claim 7 wherein said heating takes place at a rate of 0.2° to 5° C./minute.